United States Patent [19]

Agoro

[11] 4,124,724
[45] Nov. 7, 1978

[54] CRYSTALLINE CAFFEIC ACID DERIVATIVES AND COMPOSITIONS AND METHOD FOR TREATING SNAKEBITE

[76] Inventor: John W. Agoro, 4800 S. Lake Park Ave., Chicago, Ill. 60615

[21] Appl. No.: 744,891

[22] Filed: Nov. 29, 1976

Related U.S. Application Data

[63] Continuation-in-part of Ser. No. 638,919, Dec. 8, 1975, abandoned.

[51] Int. Cl.$^2$ .............................................. C07L 69/76
[52] U.S. Cl. ....................................... 424/317; 560/75
[58] Field of Search ...................... 260/473 S; 560/75; 424/317

[56] References Cited

U.S. PATENT DOCUMENTS

| | | | |
|---|---|---|---|
| 2,863,909 | 12/1958 | Panizzi et al. | 260/473 S |
| 2,918,477 | 12/1959 | Alberti | 260/473 S |
| 3,068,148 | 12/1962 | Freedmen et al. | 424/317 |

Primary Examiner—Paul J. Killos

Attorney, Agent, or Firm—Dressler, Goldsmith, Clement, Gordon & Shore, Ltd.

[57] ABSTRACT

Novel crystalline products of manufacture are represented by the formula:

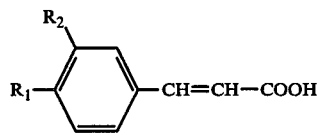

wherein $R_1$ and $R_2$ are selected from the group consisting of hydroxyl and the caffeoyl group, with the limitation that only one of $R_1$ and $R_2$ can be hydroxyl, and the pharmaceutically acceptable salts of the indicated compounds. The compounds are useful as anti-venom agents for hemolytic snake venoms. Pharmaceutical preparations containing the above compounds, or the compound commonly known as caffeic acid wherein both $R_1$ and $R_2$ are hydroxyl, are provided for treatment of snakebite victims, as well as the method of using those preparations in such treatment.

24 Claims, No Drawings

CRYSTALLINE CAFFEIC ACID DERIVATIVES AND COMPOSITIONS AND METHOD FOR TREATING SNAKEBITE

CROSS-REFERENCE TO RELATED APPLICATION

This application is a continuation-in-part of my co-pending application Ser. No. 638,919, filed Dec. 8, 1975, now abandoned.

BACKGROUND OF THE INVENTION

Presently available treatments for snakebite suffer from a number of disadvantages, all of which are avoided by the present invention.

Prior to the introduction of anti-venoms, the most commonly used treatment for snakebite was incision and suction. Prompt incision-suction can remove lethal amounts of venom, and in some cases where medical treatment is unavailable a sufficient amount of venom may be removed to be lifesaving. However, this method has not always been effective. In severe cases, amputation, including amputation by self-treatment, has been necessary. Tourniquets may be employed, alone or with incision and suction, as a temporary measure by persons who have suffered a snakebite and are remote from convenient medical help.

The presently preferred treatment for snakebit, if medical help is available, is the use of anti-venom. Natural venom contains all the antigens of a given venom and therefore produces the best anti-venoms or anti-serums to the toxins contained in snake venom. The currently available anti-venoms are generally prepared by injecting the venom of a given snake into horses and extracting the anti-venom produced therefrom from the horse serum. However, the use of anti-venoms suffers from a number of serious disadvantages.

Administration of anti-venoms must always be by intravenous drip. Serum sensitivity first has to be assessed by injecting diluted horse serum obtained, for example, from Wyeth Pharmaceutical Company or similar sources or by administering 0.2 ml of undiluted anti-venom subcutaneously. If the snakebite victim exhibits sensitivity, slow administration of anti-venom is necessary, along with concurrent administration of massive dosages of glucocorticoids and large doses of antihistamines such as cyproheptadine, trimeprazine, or methdilazine. Since all of the above-named potent antihistamines also possess significant antiserotonin activity, they may also have to be given intravenously. Ephinephrine may also be required. In other words, the snakebite victim must be hospitalized in order to receive proper treatment. Even with careful medical attention, serum sickness is common after anti-venom administration. Therefore there has been a longstanding need for a less toxic treatment for snakebite.

The ideal anti-snake venom agent would be one which could be administered orally and thus could be taken by the snakebite victim at the time he receives the bite. It would also be highly desirable to provide an agent which could be administered prior to a potential victim's exposure to snakebite and which would protect him from subsequent snakebite. The present invention provides such agents.

The ground roots of the plants Berkheya spekeana and Echinops amplexicaulis, both of the compositae family, have been used as anti-snake venom treatment by a limited number of people living in a part of East Africa who kept the remedy secret. It has not been possible prior to this invention to provide controlled dosages of the active factors in the roots and to eliminate the side effects of the other materials in the roots.

SUMMARY OF THE INVENTION

According to the present invention, it has unexpectedly been found that novel crystalline products of manufacture of the formula:

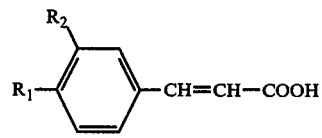

wherein $R_1$ and $R_2$ are selected from the group consisting of hydroxyl and the caffeoyl group, with the limitation that only one of $R_1$ and $R_2$ can be hydroxyl, as well as the pharmaceutically acceptable salts of the indicated products, are useful as anti-snake venom agents when the venom is a hemolytic toxin. As a part of this invention, it has been found that these crystalline products can be isolated in the pure form from the roots of the Berkheya spekeana and Echinops amplexicaulis plants.

The pharmaceutical compositions provided by this invention additionally include the known compound caffeic acid, in which $R_1$ and $R_2$ are both hydroxyl, and its pharmaceutically acceptable salts.

The method of treating snakebite victims that is provided by this invention utilizes the indicated pharmaceutical compositions, administered either orally or parenterally.

The crystalline products of manufacture and the pharmaceutical compositions containing such products provided by the present invention have a number of advantages over the currently used anti-venom. The compounds are orally active, and can be administered either prior to exposure to snakebite or after the victim has been bitten. Another important advantage of the novel products and compositions provided by this invention is their lack of toxicity. It is surprising that the novel crystalline products of manufacture are effective against snakebites, since they account for less than 1% of the weight of the ingredients in the dried roots of the above-named plants.

When used for treatment after a snakebite has occurred, the crystalline products of manufacture of this invention are generally administered to a mammalian host as an anti-snake venom agent in oral or parenteral dosages of from 0.0005 to 0.05 mg/kg of body weight until the effects of the snake venom have been countered. Administration is preferably oral, although the compounds are active when administered parenterally. When administered prior to exposure to snakebite, the products can be administered in oral or parenteral dosages of approximately the same dosages as just indicated.

The crystalline products of manufacture of this invention are:
3-hydroxy-4-(3',4'-dihydroxycinnamoyl)-cinnamic acid
4-hydroxy-3-(3',4'-dihydroxycinnamoyl)-cinnamic acid
3,4-di-(3',4'-dihydroxycinnamoyl)-cinnamic acid The term "caffeoyl caffeic acid" is used in this specification and the appended claims to mean either of the first two compounds just listed, or a mixture thereof.

The compound 3,4-dihydroxycinnamic acid, commonly designated caffeic acid, is included in the compounds useful as an active agent in the pharmaceutical compositions of this invention. The crystalline products isolated from the roots of the Berkheya spekeana and Echinops amplexicaulis plants are dimers and the trimer of caffeic acid. The dimers can be utilized in their optically pure forms or as mixtures of the isomers.

The term "caffeoyl group" as used in this specification and the appended claims refers to the group of the formula:

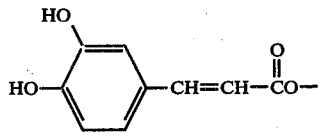

The term "pharmaceutically acceptable salts" refers to the non-toxic alkali metal, alkaline earth metal, and ammonium salts commonly used in the pharmaceutical industry, and includes the sodium, potassium, calcium, magnesium, and ammonium salts which are prepared by methods well known in the art. The term as used herein includes the mono- and di- cationic salts, although additional poly- salts may be formed. Thus, included within the crystalline products of this invention are, for example, the sodium salt of caffeoyl caffeic acid, the magnesium salt of 3-hydroxy-4-(3',4'-dihydroxycinnamoyl)-cinnamic acid, the potassium salt of 4-hydroxy-3-(3',4'-dihydroxycinnamoyl)-cinnamic acid, the calcium salt of caffeoyl caffeic acid, the ammonium salt of 3,4-di-(3',4'-dihydroxycinnamoyl)-cinnamic acid, and the like.

The novel crystalline products of manufacture of this invention can be prepared by extraction and purification from the appropriate plant roots, or can be chemically synthesized. Dimerization of caffeic acid can be easily accomplished by dissolving equimolar amounts of caffeic acid and N,N'-dicyclohexylcarbodiimide in pyridine and ether, respectively, refluxing the mixture for three days, reducing the volume of the mixture and separating the crystalline products by column or paper chromatography. The trimer, obtained as a by-product of the above reaction, is recovered in the first fraction.

DETAILED DESCRIPTION OF THE PREFERRED EMBODIMENTS

This invention provides novel crystalline products of manufacture which are useful as anti-snake venom agents and are represented by the formula:

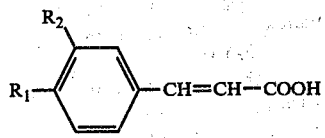

wherein $R_1$ and $R_2$ are selected from the group consisting of hydroxyl and the caffeoyl group, with the limitation that only one of $R_1$ and $R_2$ can be hydroxyl, and the pharmaceutically acceptable salts of the indicated compounds.

The crystalline products of manufacture of this invention are the dimers and the trimer of 3,4-dihydroxycinnamic acid, commonly known as caffeic acid. These novel crystalline products of manufacture and caffeic acid are the active agents in the pharmaceutical compositions of this invention, which are useful as anti-snake venom agents against venoms having hemolytic toxicity.

Caffeic acid and the crystalline products of manufacture disclosed herein are generally administered to a mammalian host which has been exposed to a hemolytic snake venom, in oral or parenteral dosages of from 0.0002 to 0.05 mg/kg of body weight. Specifically, protection is afforded, in the case of caffeic acid, by treating a human or other mammalian patient of from 0.0005 to a total of 0.05 mg/kg of body weight, and preferably 0.005 to 0.05 mg/kg following snakebite, and thereafter discontinuing treatment for at least one month, and resuming treatment only if the patient expects to be exposed to possible snakebite again, i.e. the patient is a herpetologist, reptile keeper in a zoo, an archeologist working in snake infested areas, cattle, dogs or cowboys in rattlesnake country, and the like. Experiments in test animals have established protection lasts at least one month, therefore, based on present data, herpetologists, etc. should take reinforcing doses of caffeic acid at one month intervals or less frequently as tests indicate.

3-hydroxy-4-(3',4'-dihydroxycinnamoyl)-cinnamic acid, 4-hydroxy-3-(3',4'-dihydroxycinnamoyl)-cinnamic acid and 3,4-di-(3',4'-dihydroxycinnamoyl)-cinnamic acid are administered in dosages of from 0.0002 to 0.02 mg/kg of body weight until the effects of the venom have been overcome and preferably in dosages of 0.002 to 0.02 mg/kg following snakebite or prior to possible exposure thereto, although dosages as high as 0.05 mg/kg of any of the agents of this invention can be administered following snakebite or prior to exposure thereto.

While oral administration is the preferred route of administration, dosage forms suitable for parenteral administration, i.e., intramuscular, intraperitoneal or intravenous administration, are provided for those instances where the snakebite victim is unable to take the preparation in oral form, i.e., the victim is unconscious or for any other reason is unable to swallow.

As stated above, protection is afforded by administering caffeic acid or a crystalline product of manufacture of this invention, or a pharmaceutically acceptable salt thereof, either prior to or after exposure to the venom. Thus, a person who is likely to be exposed to snakebite can preferably receive prophylactic treatment prior to possible exposure, or can carry oral compositions, i.e., tablets or capsules, in a medicine kit and take the medication immediately after being bitten.

The compounds disclosed herein as novel crystalline products of manufacture, which are also included in the pharmaceutical compositions of this invention, are:
3-hydroxy-4-(3',4'-dihydroxycinnamoyl)-cinnamic acid ($R_1$ = caffeoyl, $R_2$ = hydroxyl), decomp. 135°–140° C.
4-hydroxy-3-(3',4'-dihydroxycinnamoyl)-cinnamic acid ($R_1$ = hydroxyl, $R_2$ = caffeoyl), decomp. 135°–140° C.
3,4-di-(3',4'-dihydroxycinnamoyl)-cinnamic acid ($R_1$ = $R_2$ = caffeoyl).

The pharmaceutical compositions of this invention include in addition to these novel crystalline products of manufacture the known compound in which both $R_1$ and $R_2$ are hydroxyl, 3,4-dihydroxy-cinnamic acid, commonly known as caffeic acid, decomp. 223°–225° C.

The crystalline products of manufacture of this invention can be obtained by purification of the root extract according to Example 1 below. Dimerization of caffeic acid to produce the first two compounds listed just above can also be accomplished as described in Example 2 by refluxing caffeic acid with an excess of a suitable condensing agent, such as, N,N'-dicylohexyl-carbodiimide for from about 48 to 72 hours, and separating the resulting crystalline products by column or paper chromatography. Some trimerization accompanies the dimerization, resulting in a small amount of the third compound listed just above.

Caffeic acid is commercially available and can be prepared by acid hydrolysis of chlorogenic acid according to the method of Fiedler, *Aryneimithel-Forsh:*4, p. 41 (1951) or can be synthesized by the condensation of protocatechuic aldehyde with malonic acid according to the method reported by Posner, *J. Prakt. Chem.*, 82, p. 432 (1910) or that of Hayduck, *Ber.* 36, p. 2935 (1903).

The following examples will further illustrate this invention:

EXAMPLE 1

Preparation of Crystalline Dimers of Caffeic Acid from Root Extract 100 g. of ground, dried root of the Echinops amplexicaulis plant was taken up in 300 ml. of methanol (90% in water), refluxed for 1 hr. and filtered using #42 Whatman paper and a Büchner funnel. The procedure was repeated 2 more times and the combined solutions were absorbed on 10 g. of nylon powder and evaporated to dryness using a rotary evaporator. The dried material was then successively extracted with water to obtain Fraction A, 25% methanol to obtain Fraction B, 50% methanol to obtain Fraction C which yielded the major amount of the dimer, and finally with 100% methanol to obtain Fraction D which contained the bulk of the caffeic acid.

The active fractions were identified in vitro using commercially prepared synthetic substrates and purified rattlesnake venom phosphodiesterase, obtained from Sigma Chemical Co., P.O. Box 14508, St. Louis, Mo., according to the method of Koerner, J. F. and Sinsheimer, R. L., *J. Biol. Chem.* 228, 1049 (1975) using thymidine-5'-monophospho-p-nitrophenyl phosphate as the substrate instead of calcium bis(p-nitrophenyl) phosphate.

Active Fraction C was then subjected to paper chromatography as follows:

Fraction C was refrigerated for 1 week and then centrifuged at 18,000 r.p.m. for 30 minutes. The precipitate was discarded. Water was added to the supernatant, and the methanol was removed from the resulting solution by use of a rotary evaporator. The solution was then lyophilized to remove the water. The dried material was dissolved in 3.0 ml. of methanol and chromatographed on #3 Whatman ascending paper using a 4:1:5 mixture of ethyl formate-acetic acid-toluene as the wash. Two fractions were obtained.

The first fraction was subjected to column chromatography, after elution of the dried Whatman paper with methanol and concentrating the solution to approximately 3 ml., using butanol-acetic acid-water (6:1:4) as the eluent. The dried paper was eluted with about 95% methanol and the solution was allowed to stand for 3 days in a refrigerator and centrifuged at 18,000 r.p.m. for 30 minutes. The precipitate was discarded. The supernatant was subjected to rotary evaporation to remove the methanol and lyophilized to remove water. The resulting dry material was taken up in 0.5 ml. of methanol, chromatographed on a strip of #3 Whatman paper and eluted with ethyl formate-acetic acid-toluene (4:1:5) to yield approximately 50 mg. of 3-hydroxy-4-(3',4'-dihydroxycinnamoyl)-cinnamic acid, decomp. 135°–140° C., approximately 12.0 mg. of 4-hydroxy-3-(3',4'-dihydroxycinnamoyl)-cinnamic acid, decomp. 135°–140° C., and approximately 20 mg. of residual caffeic acid.

EXAMPLE 2

Synthesis of Crystalline Dimers and Trimer of Caffeic Acid

A solution of 1.701 g. of N,N'-dicyclohexylcarbodiimide dissolved in 50 ml. of dry ether was slowly added to a solution of 1.701 g. of caffeic acid dissolved in 150 ml. of pyridine with stirring. The reaction mixture was refluxed for 3 days at 120° C. The reaction mixture was cooled in an ice bath, whereupon crystallization occurred. The solution was separated by filtration and washed 4 times with ether.

The volume of the supernatant was reduced using a rotary evaporator while warming. The reaction mixture was again cooled in an ice bath and the resulting crystallization material was separated by filtration using an ether wash.

The supernatant was concentrated by rotary evaporation and the concentrate was layered on a 15 cm. × 2.5 cm. column of Sephadex L-H20 gel and eluted with methanol. Fraction 1 contained the trimer, 3,4-di-(3',4'-dihydroxycinnamoyl)-cinnamic acid, obtained as a viscous liquid.

Fraction 2 contained a mixture of caffeic acid and its isomeric dimers. Fraction 2 was chromatographed on a #3 Whatman paper strip and eluted with ethyl formate-acetic acid-toluene (4:1:5). Fraction 2a contained the isomeric dimers and Fraction 2b contained the caffeic acid.

Fraction 2a was chromatographed on #3 Whatman paper, eluting with butanol-acetic acid-water (6:1:4) to separate any remaining caffeic acid. The eluate was concentrated and chromatographed on #3 Whatman paper. Elution with ethyl formate-acetic acid-toluene (4:1:5) produced the two isomers of the dimer in the following amounts: 73 mg. of 3-hydroxy-4-(3',4'-dihydroxycinnamoyl)-cinnamic acid, decomp. 135°–140° C. and 68 mg. of 4-hydroxy-3-(3',4'-dihydroxycinnamoyl)-cinnamic acid, decomp. 135°–140° C. The structural identity of the compounds was confirmed using ultraviolet scanning and nuclear magnetic resonance (NMR).

EXAMPLE 3

In Vitro Determination of the Activity of Caffeic Acid, 3-hydroxy-4-(3',4'-dihydroxycinnamoyl)-cinnamic acid, and 4-hydroxy-3-(3',4'-dihydoxycinnamoyl)-cinnamic acid (a) Mixtures of 20 μg. of rattlesnake venom phosphodiesterase (Sigma Chemical Co., P.O. Box 14508, St. Louis, Mo.), 0.1 M tris-acetic acid buffer, pH 8.9, 0.1 M magnesium chloride and 2 μg. of each of the above compounds were prepared. (Rattlesnake venom is generally classified as a hemolytic type toxin.) Each of the mixtures was incubated at 41° C. for 10 minutes using a $10^{-4}$ M thymidine-5'-monophospho-p-nitrophenyl ester as the substrate, following the procedure described in Koerner et al., *J. Biol. Chem.* 228, 1049 (1975). After the incubation period, 0.5 M sodium hydroxide was added to stop the reaction. The material was centrifuged for 10 minutes and the supernatants of each of the degraded products were read at 400 nm. spectrometrically.

Results: 2 μg. of both 3-hydroxy-4-(3',4'-dihydroxy cinnamoyl)-cinnamic acid, and 4-hydroxyl-3-(3',4'-dihydroxy, cinnamoyl)-cinnamic acid inhibited the venom effect 100%. 2 μg. of caffeic acid inhibited the venom effect by 60-80%.

(b) The same levels of each compound and venom used in 3a, supra, were incubated with egg yolk suspended in normal saline solution. Venom failed to hydrolyze egg yolk in the presence of each of the above compounds.

(c) Similarly, venom and lecithin added to a suspension of human red blood cells containing the above levels of each compound failed to hemolyze the red blood cells in the presence of the compounds.

EXAMPLE 4

In Vivo Evaluation of Caffeoyl Caffeic Acid 40 rats weighing approximately 180 grams each were divided into four groups of 10 rats each. Group I rats received 9.0 mg. of purified rattlesnake venom alone, obtained from Sigma Chemical Co., which is in excess of the lethal dosage. Group II rats received 9.0 mg. of purified rattlesnake venom and 0.36 μg. orally of crystalline caffeoyl caffeic acid. Group III rats received 0.36 μg. orally of crystalline caffeoyl caffeic acid alone. Group IV control rats received no venom or drug.

Results:

Group I rats died within 15 minutes of receiving the venom.

Group II rats survived and lived a normal life span.

Group III rats remained as normal as Group IV rats and appeared to suffer no toxic effects from the drug.

One month following the drug treatment just described, the Group II rats were injected with 9.0 mg. of purified rattlesnake venom, but received no further drug. The rats were unaffected by the venom.

EXAMPLE 5

In Vivo Evaluation of 3,4-di-(3',4'-dihydroxycinnamoyl)-cinnamic Acid 40 rats weighing approximately 180 grams each were divided into four groups of 10 rats each. Group I rats received 9.0 mg. of purified rattlesnake venom alone, obtained from Sigma Chemical Co., which is in excess of the lethal dosage. Group II rats received 9.0 mg. of purified rattlesnake venom and 0.26 μg. orally of the crystalline trimer 3,4-di-(3',4'-dihydroxycinnamoyl)-cinnamic acid. Group III rats received 26 μg. orally of the trimer alone. Group IV rats were the control group, and received no venom or drug.

The results were identical with those obtained with caffeoyl caffeic acid:

Group I rats died within 15 minutes of receiving the venom.

Group II treated rats survived and lived a normal life span.

Group III rats remained as normal as Group IV rats and appeared to suffer no toxic effects from the drug.

One month following the drug treatment just described, the Group II rats were injected with 9.0 mg. of purified rattlesnake venom, but received no further drug. The rats were unaffected by the venom.

EXAMPLE 6

In Vivo Evaluation of Crystalline Caffeic Acid 40 rats weighing approximately 180 grams each were divided into four groups of 10 rats each. Group I rats received 9.0 mg. of purified rattlesnake venom alone, obtained from Sigma Chemical Co., which is in excess of the lethal dosage. Group II rats received 9.0 mg. of purified rattlesnake venom and 0.87 μg. orally of crystalline caffeic acid. Group III rats received 0.87 μg. orally of crystalline caffeic acid alone. Group IV rats were the control group, and received no venom or drug.

Similar results were obtained with caffeic acid:

Group I rats died within 15 minutes of receiving the venom.

Group II treated rats survived and lived a normal life span.

Group III rats remained as normal as Group IV rats and appeared to suffer no toxic effects from the drug.

One month following the drug treatment just described, the Group II rats were injected with 9.0 mg. of purified rattlesnake venom, but received no further drug. The rats were unaffected by the venom.

As is seen from the results of Examples 4-6, respectively, the dimer, the trimer, and caffeic acid are all effective in inhibiting the hemolytic action of snake venom. Other experimental work indicates that of these three compounds, the trimer is most effective, and the dimer the next most effective, for the indicated purpose.

Caffeic acid and the crystalline products of manufacture of this invention are generally formulated into pharmaceutical compositions comprising, as an active ingredient, at least one of the active anti-snake venom agents in association with a pharmaceutical carrier or diluent. Caffeic acid and the crystalline products useful in the practice of this invention exhibit both oral and parenteral activity and can be formulated in dosage forms suitable for oral or parenteral administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate, sweetening and flavoring agents, and the like. In the case of capsules, for example, the active agent may be the sole ingredient.

Liquid dosage forms for oral administration include pharmaceutically acceptable emulsions, solutions, suspensions, syrups, and elixirs containing inert diluents commonly used in the art, such as water. Besides inert diluents such compositions can also include adjuvants such as wetting agents, emulsifying and suspending agents, and sweetening, flavoring and perfuming agents.

Preparations according to this invention for parenteral administration include sterile aqueous or non-aqueous solutions, suspensions of emulsions. Examples of non-aqueous solvents or vehicles are propylene glycol, polyethylene glycol, vegetable oils such as olive and peanut oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, or by heating the compositions. They can also be manufactured in the form of sterile solid compositions which can be dissolved in sterile water, or some other sterile injectable medium immediately before use.

The dosage of active ingredients in the compositions of this invention may be varied. However, it is necessary that the amount of the active ingredient shall be such that a suitable dosage form is obtained. Generally, scored tablets containing from 0.1 to 1 mg. of active ingredient are preferred, however, the selected dosage depends upon the desired therapeutic effect, on the route of administration, and on the duration of the treatment.

EXAMPLE 7

Tablet Formulation Containing 3-hydroxy-4-(3',4'-dihydroxycinnamoyl)-cinnamic acid A tablet weighing 50 mg. and having the following composition is formulated:

| | |
|---|---|
| 3-hydroxy-4-(3',4'-dihydroxy-cinnamoyl)-cinnamic acid | 0.5 mg. |
| lactose | 23.0 mg. |
| gelatin | 1.0 mg. |
| starch | 20.0 mg. |
| magnesium stearate | 0.3 mg. |
| talcum | 5.2 mg. |

EXAMPLE 8

Tablet Formulation Containing Caffeic Acid

A tablet weighing 35 mg. and having the following composition is formulated:

| | |
|---|---|
| caffeic acid | 1.0 mg. |
| lactose | 15.0 mg. |
| gelatin | 0.5 mg. |
| starch | 10.0 mg. |
| magnesium stearate | 0.5 mg. |
| talcum | 3.0 mg. |

EXAMPLE 9

Injectable Formulation Containing 3,4-di-(3',4'-dihydroxycinnamoyl)-cinnamic acid A sterile ampoule is prepared in the conventional manner containing 0.5 mg. of 3,4-di-(3',4'-dihydroxycinnamoyl)-cinnamic acid suspended in 1 ml. of peanut oil.

The above detailed description of this invention has been given for clarity of understanding only. No unnecessary limitations are to be understood therefrom, as modifications will be obvious to those skilled in the art.

With respect to caffeic acid, the foregoing in vitro and in vivo evaluations are conducted with an isomeric mixture of the cis and trans isomers of caffeic acid. The mixture, which was also purchased from a commercial source, Aldrich Chemical Company, Milwaukee, Wisconsin, is predominately the trans isomers. In order to evaluate the relative anti-snake venom activity of the cis and trans isomers of caffeic acid, a comparison in vitro according to the method set forth in Example 3 as follows:

EXAMPLE 10

In Vitro Determination Of The Relative Activities Of Caffeic Acid, Cis-Caffeic Acid and Trans-Caffeic Acid Mixtures of 20 μg of rattlesnake venom phosphodiesterase (Sigma Chemical Co., P.O. Box 14508, St. Louis, Mo.), 0.1 M tris-acetic acid buffer, pH 8.9, 0.1 M magnesium chloride and 1 μg. of each of the above compounds were prepared. (Rattlesnake venom is generally classified as a hemolytic type toxin.) Each of the mixtures was incubated at 41° C. for 10 minutes using a $10^{-4}$ M thymidine-5'-monophospho-p-nitrophenyl ester as the substrate, following the procedure described in Koerner et al., J. Biol. Chem. 228, 1049 (1975). After the incubation period, 0.5 M sodium hydroxide was added to stop the reaction. The material was centrifuged for 10 minutes and the supernatants of each of the degraded products were read at 400 nm. spectrometrically.

One μg. of the isomeric mixture of cis and trans caffeic inhibited the venom effect by 40.9%. One μg of trans caffeic acid inhibited the venom effect by 86.9%. One μg of cis-caffeic acid inhibited the venom effect by 2.6%. The cis isomer of caffeic acid utilized in Example 10 was prepared by subjecting the material obtained from Aldrich Chemical Company to ultraviolet light according to the method described by Haskins and Gorz, Archives of Biochemical and Biophysics 81, pp. 204–210 (1959). The commercially available material is obtained in an opaque bottle to prevent conversion of trans isomer to the cis isomer during storage.

Thus the anti-snake venom activity of caffeic acid is believed to reside solely in the trans isomer, and while it is preferred to utilize trans-caffeic acid in the practice of this invention when caffeic acid is employed as the anti-snake venom agent, the isomeric mixture can be employed so long as a therapeutically effective amount of the trans isomer is provided.

What is claimed is:

1. A crystalline product of manufacture of the formula:

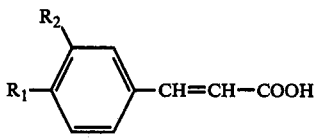

wherein $R_1$ and $R_2$ are selected from the group consisting of hydroxyl and the caffeoyl group, with the limitation that only one of $R_1$ and $R_2$ can be hydroxyl, and the pharmaceutically acceptable salts thereof.

2. A crystalline product in accordance with claim 1 of the formula:

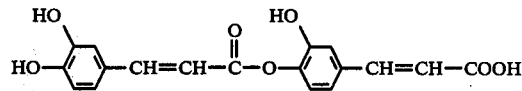

and the pharmaceutically acceptable salts thereof.

3. A crystalline product in accordance with claim 1 of the formula:

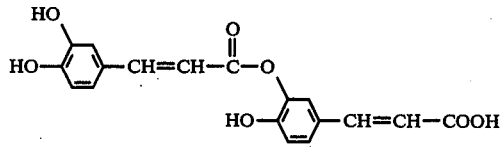

and the pharmaceutically acceptable salts thereof.

4. A crystalline product in accordance with claim 1. that is a mixture of compounds of the formula:

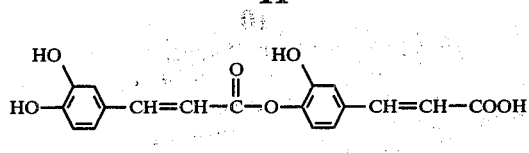

and

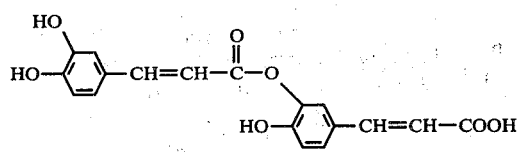

and the pharmaceutically acceptable salts thereof.

5. A crystalline product in accordance with claim 1 of the formula:

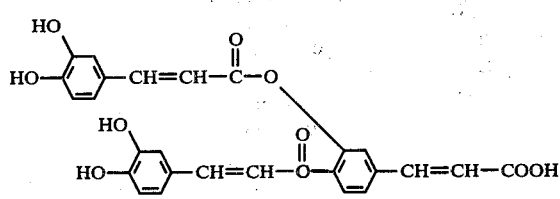

and the pharmaceutically acceptable salts thereof.

6. A crystalline product of manufacture consisting of a member selected from the group consisting of caffeoyl caffeic acid, decomp. 135°–140° C., and the pharmaceutically acceptable salts thereof.

7. A crystalline product of manufacture consisting of a member selected from the group consisting of 3-hydroxy-4-(3',4'-dihydroxycinnamoyl)-cinnamic acid and the pharmaceutically acceptable salts thereof.

8. A crystalline product of manufacture consisting of a member selected from the group consisting of 4-hydroxy-3-(3',4'-dihydroxycinnamoyl)-cinnamic acid and the pharmaceutically acceptable salts thereof.

9. A crystalline product of manufacture consisting of a member selected from the group consisting of 3,4-di-(3',4'-dihydroxycinnamoyl)-cinnamic acid and the pharmaceutically acceptable salts thereof.

10. A pharmaceutical preparation suitable for oral or parenteral use comprising a therapeutically effective amount of anti-snake venom drug selected from the group consisting of a crystalline product of manufacture of the formula:

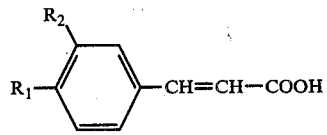

wherein $R_1$ and $R_2$ are the same or different members of the group consisting of hydroxyl and the caffeoyl group, with the limitation that only one of $R_1$ and $R_2$ can be hydroxyl, a mixture of said products, and pharmaceutically acceptable salts of said products, together with a pharmaceutically acceptable carrier or diluent.

11. A pharmaceutical preparation in accordance with claim 10 compounded for oral use.

12. A pharmaceutical preparation in accordance with claim 10 compounded for parenteral use.

13. A pharmaceutical preparation in accordance with claim 10 wherein said crystalline product of manufacture is 3-hydroxy-4-(3',4'-dihydroxycinnamoyl)-cinnamic acid or a pharmaceutically acceptable salt thereof.

14. A pharmaceutical preparation in accordance with claim 10 wherein said crystalline product of manufacture is 4-hydroxy-3-(3',4'-dihydroxycinnamoyl)-cinnamic acid or a pharmaceutically acceptable salt thereof.

15. A pharmaceutical preparation in accordance with claim 10 wherein said crystalline product of manufacture is 3,4-di-(3',4'-dihydroxycinnamoyl)-cinnamic acid or a pharmaceutically acceptable salt thereof.

16. A pharmaceutical preparation in accordance with claim 10 wherein said crystalline product is caffeoyl caffeic acid or a pharmaceutically acceptable salt thereof.

17. A pharmaceutical preparation suitable for oral or parenteral administration to a mammalian snakebite victim comprising from about 0.03 to about 3.5 mg. of 3,4-dihydroxycinnamic acid or a pharmaceutically acceptable salt thereof, together with a pharmaceutically acceptable carrier or diluent.

18. A pharmaceutical preparation in accordance with claim 17 wherein the trans isomer of 3,4-dihydroxy cinnamic acid is present in a dosage of from 0.03 to about 3.5 mg.

19. A method of inhibiting the hemolytic action of snake venom comprising administering to a mammalian snakebite patient a therapeutically effective amount of anti-snake venom drug selected from the group consisting of a crystalline product of manufacture of the formula:

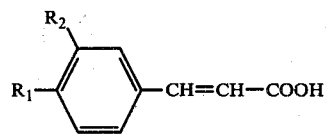

wherein $R_1$ and $R_2$ are the same or different members of the group consisting of hydroxyl and the caffeoyl group, a mixture of said products, and pharmaceutically acceptable salts thereof.

20. The method of claim 19 wherein said anti-snake venom drug is 3-hydroxy-4-(3',4'-dihydroxycinnamoyl)-cinnamic acid or a pharmaceutically acceptable salt thereof.

21. The method of claim 19 wherein said anti-snake venom drug is 4-hydroxy-3-(3',4'-dihydroxycinnamoyl)-cinnamic acid or a pharmaceutically acceptable salt thereof.

22. The method of claim 19 wherein said anti-snake venom drug is 3,4-di-(3',4'-dihydroxycinnamoyl)-cinnamic acid or a pharmaceutically acceptable salt thereof.

23. The method of claim 19 wherein said anti-snake venom drug is caffeic acid or a pharmaceutically acceptable salt thereof.

24. The method of claim 13 comprising treating said snake-bite patient with a total of from 0.03 to 3.5 mg. of caffeic acid or a pharmaceutically acceptable salt thereof and thereafter discontinuing treatment for at least one month.

* * * * *

UNITED STATES PATENT AND TRADEMARK OFFICE
CERTIFICATE OF CORRECTION

PATENT NO. : 4,124,724
DATED : November 7, 1978
INVENTOR(S) : John W. Agoro

It is certified that error appears in the above-identified patent and that said Letters Patent are hereby corrected as shown below:

Column 8, line 60: "of" (first occurrence) should be -- or --.

Column 11, in the lower part of the formula in claim 5:

$$\overset{"}{\underset{-O-}{\overset{O}{\|}}}"\ \text{should be}\ --\ \underset{-C-O-}{\overset{O}{\|}}\ --.$$

Column 11, line 34: "(3',4-dihydroxycinnamoyl)" should be -- (3'-4'-dihydroxycinnamoyl) --.

Signed and Sealed this

Twenty-second Day of May 1979

[SEAL]

Attest:

RUTH C. MASON
Attesting Officer

DONALD W. BANNER
Commissioner of Patents and Trademarks